US00PP11124P

United States Patent [19]

Fruehwirth

[11] Patent Number: Plant 11,124

[45] Date of Patent: Nov. 16, 1999

[54] POINSETTIA PLANT NAMED 'ECKADA'

[75] Inventor: Franz Fruehwirth, Encinitas, Calif.

[73] Assignee: Paul Ecke Ranch, Inc., Encinitas, Calif.

[21] Appl. No.: 09/005,642

[22] Filed: Jan. 12, 1998

[51] Int. Cl.[6] ..... A01H 5/00

[52] U.S. Cl. ..... Plt./307

[58] Field of Search ..... Plt./307

[56] References Cited

U.S. PATENT DOCUMENTS

P.P. 9,952 7/1997 Fruehwirth ..... Plt./307

*Primary Examiner*—Howard J. Locker
*Assistant Examiner*—Kent L. Bell
*Attorney, Agent, or Firm*—Arnold, White & Durkee

[57] ABSTRACT

Poinsettia 'Eckada' is a new cultivar, distinguished by dark red, upright flower bracts, dark green foliage, self-branching characteristics and 9½-week flowering response time. The new plant produces a very desirable branched flowering pot plant for the late-season holiday market. Poinsettia 'Eckada' is resistant to epinasty after being confined to shipping containers. The post-production foliage and bract retention is excellent even under low light intensities in the consumer's home.

1 Drawing Sheet

BACKGROUND OF THE PLANT

This new poinsettia cultivar, 'Eckada', originated as an induced self-branching sport of a seedling known as "P-70" (not patented) in my greenhouse in Encinitas, Calif. It was selected because of its upright, dark red flower bracts, dark green foliage, self branching characteristics, and late-season flowering response; traits that distinguish it from other poinsettia cultivars, and seem to make it a desirable plant for commercial greenhouse production. After selection, 'Eckada' was vegetatively reproduced from stem cuttings for test purposes in Encinitas, Calif. "P-70" is a proprietary plant and there are no specimens in the public domain. Poinsettia "P-70" is not self-branching in that no axillary branches develop as long as the apical bud is not removed (pinched). 'Eckada' is self-branching in that during development axillary branches elongate without removal of the apical bud. If under short day conditions, the axillary branches will develop inflorescences. By subjecting clones of this plant to successive generations of vegetative propagation, it was demonstrated that the distinctive characteristics of 'Eckada' held true from generation to generation.

BRIEF DESCRIPTION OF THE PHOTOGRAPHS

Poinsettia 'Eckada' is illustrated in the accompanying color photographs.

The upper photograph is a side view of a branched plant.

The lower photograph is a top view of the same 'Eckada' plant showing flower and bract formation.

DESCRIPTION OF THE PLANT

The following is a detailed description of this new poinsettia as observed in Encinitas, Calif., USA during December 1996. Observations were recorded from flowering plants, grown as one branched plant per pot. The pot was 14 cm in diameter and 11 cm in height. Color designations are compared to the 1986 edition of R.H.S. Colour Chart, first published in 1966 by The Royal Horticultural Society, London, England.

THE PLANT

Origin: Sport of a seedling. The sport was induced by application of the procedures set forth in U.S. Pat. No. 4,724,276 to the seedling parent plant. Rootstock used was '603' (U.S. Plant Pat. No. 9,952).

Classification:

*Botanical.*—*Euphorbia pulcherrima* Willd.

*Common name.*—Poinsettia.

*Cultivar name.*—'Eckada'.

Form: Shrub.

Height: Short — medium.

Growth habit: As a single stemmed plant, upright and vigorous with self-branching side shoots. The application of a chemical growth retardant may not be needed to restrict height for commercial pot plant production. I observed a branched plant in a pot with an overall height of 41 cm and an overall width of 54 cm. The diameter of individual inflorescences is 28 cm.

Branching: Axillary branches will develop and terminate in an inflorescence without pinching. However, it is usually desirable to pinch 'Eckada' before flower induction and remove all terminal dominance. Then, all axillary branches will develop uniformly and at a faster rate.

Growth rate: Rooting of stem cutting occurs in 12–18 days under intermittent mist. The plant will flower in about 9½ weeks under continuous long night conditions and night temperatures of about 16–18° C.

Foliage: The foliage is clean and uniformly dark green from bottom to top of the plant. The leaves are of medium size, leaf blades typically 14 cm long and 9–10 cm wide. Leaf petioles are 4 cm long and dark red. The upper leaf surface is glabrous, but slightly rugose and the under surface is finely pubescent.

*Leaf shape.*—Typical leaves are ovate with obtuse bases and acuminate tips. Leaf margins are dentate with 2 lobes on each side of the leaf blade.

*Color.*—Upper side — Dark green, much darker than R.H.S. 147A. Under side — Green, R.H.S. 147A-B.

*Retention.*—The foliage lasts extremely well even under low light intensities in the consumer's home.

Bracts: Generally there are 19–23 upright, dark red bracts of various sizes subtending the cyathia. The primary bracts have blades typically 14–15 cm long and 10 cm wide with petioles 2–3 cm long, dark red on top and reddish on the under side.

*Shape.*—Primary bracts are ovate with acute bases and acuminate tips. Primary bract margins have modest lobes. Secondary bracts are of various sizes, elliptic, and have entire margins.

*Color.*—Upper side — Dark red, near R.H.S. 46B. Under side — Red, R.H.S. 46B-C.

Flowers: Generally, 6–8 cyathia (flowers) per inflorescence are present when the plant is in full bloom. Each cyathium is about 6 mm long and 6 mm wide, green in color, and fringed red at the distal end. One yellow nectar cup protrudes from the side of each cyathium. The flower pedicel is also green and about 5 mm in length. The stamens protruding from the cyathia are red. The anthers are bifurcate; the pollen is yellow and copious. The stigmas are dark red and trifurcate.

*Nectar exudate.*—Abundant.

*Seeds.*—Self-incompatible.

*Fertility.*—Not observed.

Post production: Poinsettia 'Eckada' is resistant to epinasty after being confined to shipping containers and retains its leaves and flower bracts for several weeks in the consumer's home environment.

Disease resistance: Typical of the species.

What is claimed is:

1. A new and distinct Poinsettia plant, substantially as herein shown and described, distinguished by its upright, dark red flower bracts, dark green foliage, self-branching characteristics and late-season flowering response.

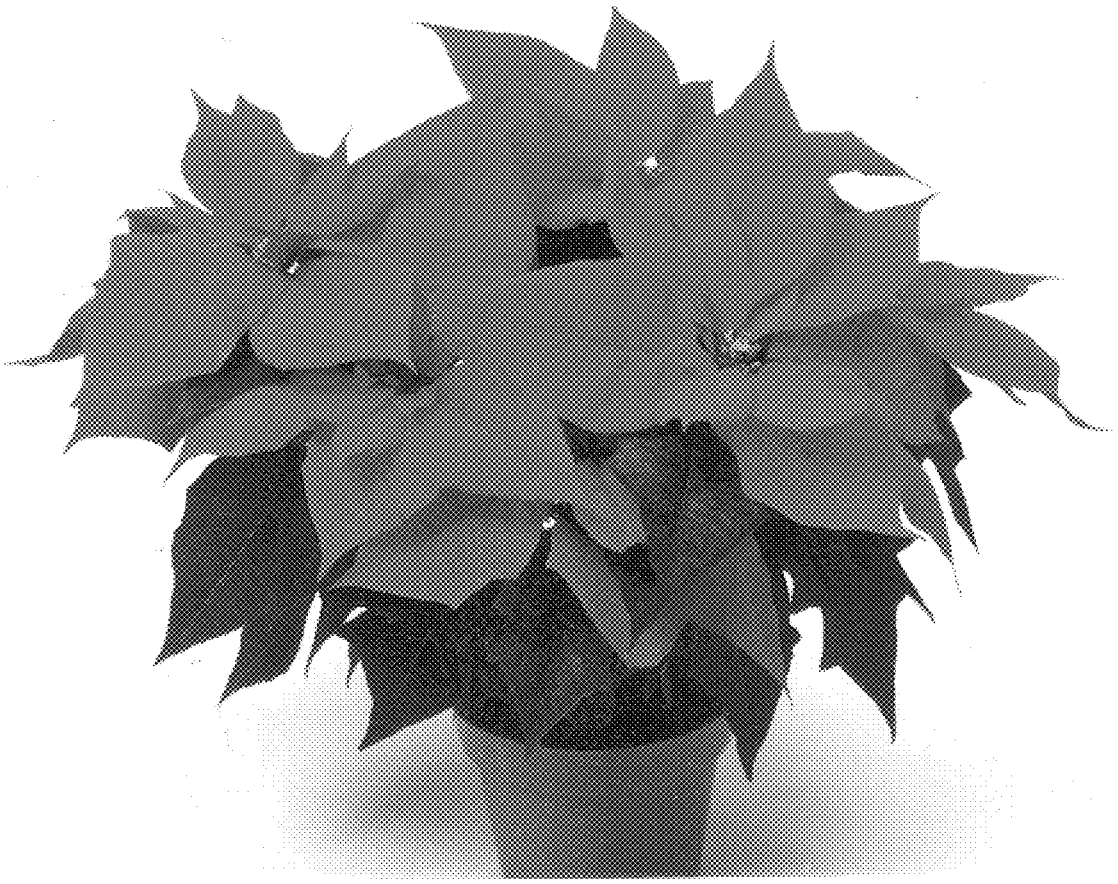
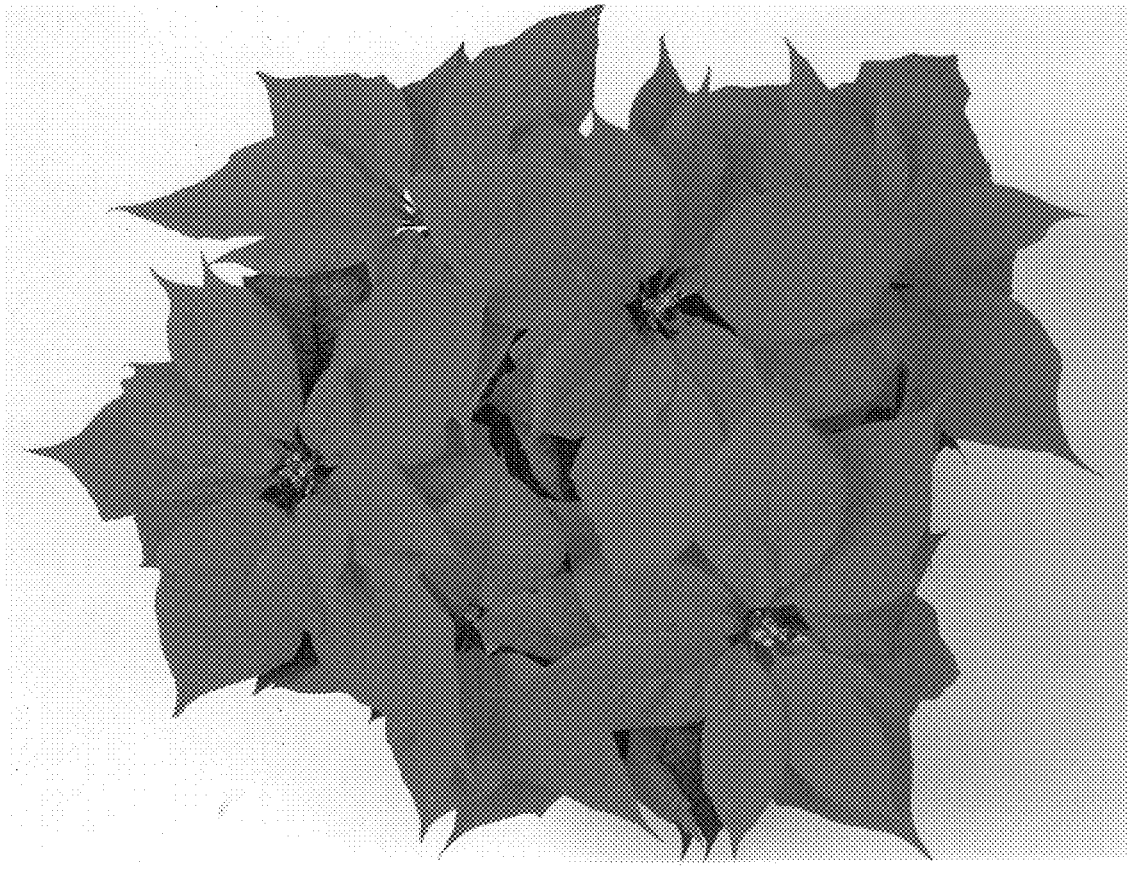

* * * * *